United States Patent [19]

Manoli

[11] 4,226,248
[45] Oct. 7, 1980

[54] PHONOCEPHALOGRAPHIC DEVICE

[76] Inventor: Samir H. Manoli, 136 Black Bay Crescent, Thunder Bay, Ontario, Canada

[21] Appl. No.: 955,029

[22] Filed: Oct. 26, 1978

[51] Int. Cl.³ .............................................. A61B 7/04
[52] U.S. Cl. ................................ 128/773; 179/1 ST; 181/131
[58] Field of Search ...................... 128/773, 746, 670; 179/1 ST; 181/131

[56] References Cited
U.S. PATENT DOCUMENTS

| 1,686,504 | 10/1928 | Dodge et al. | 128/773 X |
| 3,181,528 | 5/1965 | Brackin | 128/773 |
| 3,888,238 | 6/1975 | Meindl et al. | 128/660 |
| 4,002,161 | 11/1977 | Klar et al. | 128/746 |
| 4,008,711 | 2/1977 | Olingen et al. | 128/773 X |
| 4,029,083 | 6/1977 | Baylor | 128/746 |
| 4,079,198 | 3/1978 | Bennett | 128/746 |

FOREIGN PATENT DOCUMENTS 997512  1/1952  France ....................................... 128/773

Primary Examiner—Lee S. Cohen

[57] ABSTRACT

A portable instrument for phonocephalography is provided having a pair of ear insertable microphones of sufficient sensitivity to detect sounds from the surface and cavities of the head. An amplifier is provided for increasing the output signal from each microphone. The amplified signals from each microphone are passed through a frequency analyzer and a multiplexing oscillator for display on a two channel oscilloscope. Alternatively or additionally, the amplified signals may be displayed on a chart recorder. An ECG pickup and amplifier may additionally be provided, having input to the second channel oscilloscope, for correlating ECG signals with sounds from the ear. Such a device may be portable and provides a simple, passive, non-invasive technique for diagnosis of, for example, tinnitus and intratemporal carotid aneurysm, and permits correlation of audible sounds from the head with a patient's ECG.

12 Claims, 6 Drawing Figures

PHONOCEPHALOGRAPHIC DEVICE

BACKGROUND OF THE INVENTION

This invention relates to a portable instrument and method for phonocephalography, and more particularly relates to an auscultative device and method for passively, non-invasively monitoring sounds from the surface and cavities of the head of the patient, and where desired, correlating such sounds with a person's electrocardiograph (ECG).

Oscultation in medical practice has undergone considerable progress since development of the mono-aural stethoscope. Phonocephalography is a new term introduced for the systematic oscultation, amplification and recording of sounds from the surface and cavities of the head. Hissing, pulsating or clicking sounds can be detected by phonocephalography. Audible sounds in these cases can be divided into pulsating vascular and clicking mascular tinnitus. Pulsating vascular tinnitus has fixed frequency, synchronous with the pulse and is not affected by swallowing or opening the mouth widely. Such tinnitus will change in character by compression of the carotids. Clicking tinnitus however has a variable frequency, asynchronous with the pulse. Its character will not change on compression of the carotids, but will change on swallowing or opening the mouth. For this reason, it is desirable to correlate a patient's ECG with audible sounds from the surface and cavities of the head. For instance different sounds of patients with red tumour complaining of tinnitus, patients with hypertension complaining of tinnitus, and patients with palatal myoclonus, can be identified and recorded all in correlation with ECG. Also aneurysmal dilation in a major vessel, e.g. the carotid artery, can be detected by audible sounds from the ear and correlated with the ECG. Moreover patients with carotid cavernous fistula can be detected. As far as is known by the applicant, there is no previous unitary phonocelographic device for obtaining information of the type in question. Such information in the past has been recorded by combining different and several pieces of equipment together such as microphones, audio frequency spectrometers, sound recorders, etc.

It should be noted that there are substantial differences between a phonocephalographic device such as that described in the present application and echocephalographic devices which are described in patents such as Canadian Pat. No. 973,632 of Hudson, et. al., issued Aug. 26, 1975; Canadian Pat. No. 970,462 of J. B. Williams, issued July 1, 1975. A phonocephalographic device is intended to record audible sounds from the head cavities (the ear for example)-sounds such as hissing, tinnitus, for example. Echocephalographic devices however are concerned with brain waves and use ultrasonic techniques which involve transmitting signals and recording echoes reflected from the brain. Thus the information as well as the type of signals received by these two types of devices are substantially different in nature and operation.

U.S. Pat. No. 4,008,711 of Olinger, et. al., issued Feb. 22, 1977, describes a device which monitors characteristic sounds emanated externally from the head by intracranial aneurysms. The device in question uses a microphone for picking up characteristic sound waves through a patient's closed eye lid, converting them into electric signals which are filtered, amplified, filtered again and recorded on one channel of a magnetic tape and correlated with audible heart signals which are recorded on another channel of the tape.

Other patents, of general background interest, are U.S. Pat. No. 3,990,435 of Murphy, issued Nov. 9, 1976; U.S. Pat. No. 3,653,373 of Batterman, issued Apr. 4, 1972 and U.S. Pat. No. 3,181,528 of Brackin, issued May 4, 1965.

It is an object of the present invention to provide a device for the monitoring and diagnosis of sounds from the surface and cavities of the head which will enable simple, passive, non-invasive cerebrial angiology. It is a further object of the present invention to provide a portable unitary instrument which will serve such a purpose. It is a further object of the present invention to provide a device which will enable correlative monitoring and recording of such sounds with a patient's ECG. These and other objects of the invention will be understood from the following description of the invention.

SUMMARY OF THE INVENTION

In accordance with the present invention there is provided a portable instrument for a phonocephalography having an ear insertable microphone (preferably a pair) of ear insertable microphones of sufficient sensitivity, when inserted in a patient's ears, to detect sounds from the surface and cavities of head. An amplifier is provided for increasing the output signal from each microphone. The amplified signals from each microphone are filtered through a frequency analyzer and optionally passed through a multiplexing oscillator for display on an oscilloscope. Alternatively or additionally, the amplified filtered signals may be displayed on a chart recorder. An ECG pickup and amplification means may additionally be provided, having input to the oscilloscope, for correlating ECG signals with sounds from the ear. Such a device may be portable and provides a simple, passive, non-invasive technique for diagnosis of, for example, tinnitus and intratemporal carotid aneurysm, and permits correlation of audible sounds from the head with a patient's ECG.

When combined with a patient's ECG, the sounds recorded are usually synchronous with the T wave and the T-P interval of the ECG.

BRIEF DESCRIPTION OF THE DRAWINGS

Other objects and advantages of the present invention will become apparent upon reading the following detailed description and upon referring to the drawings in which.

In the drawings similar features will be given similar reference numerals.

While the invention will be described in connection with example embodiments thereof, it will be understood that it is not intended to limit the invention to such embodiment. On the contrary, it is intended to cover all alternatives, modifications and equivalents as may be included within the spirit and scope of the invention as defined by the appended claims.

DETAILED DESCRIPTION OF THE INVENTION

Figure 1:
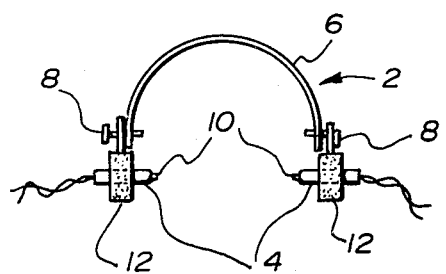
FIG. 1 is a schematic diagram of a microphone headset according to the present invention.
Figure 2:
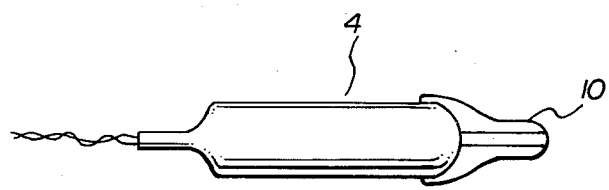
FIG. 2 is a side view of a ear insertable microphone which may be used with the device of the present invention.

Turning to FIGS. 1 and 2, there is shown a headset 2 and microphones 4 according to the present invention. The headset has a band 6 for securing the headset in position on the patient's head. Adjustable screws 8 permit sideways adjustment of the microphone to enable comfortable but sufficient insertion of ear pieces 10 in the patient's ear. The microphone is preferably a miniaturized condenser microphone, for example of one-half inch diameter; ear piece 10 is for example of one-quarter inch diameter and one-half inch length, appropriately mounted on the tip of the microphone as shown in FIG. 2. The microphone headset of FIG. 1 is also provided with a foam pad 12 or other appropriate means around the microphones to reduce extraneous noise reaching the microphones through ear pieces 10.

Figure 3:
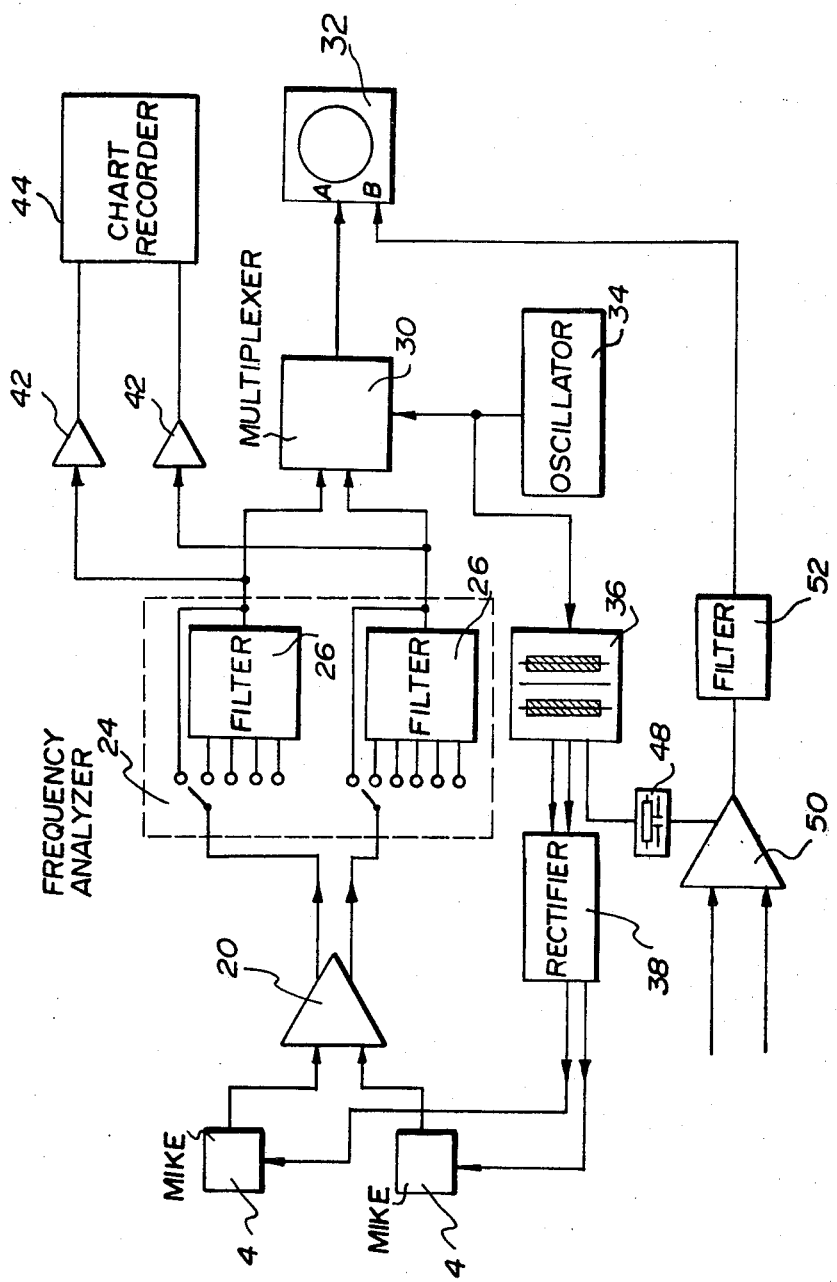
FIG. 3 is a diagrammatic illustration of a sound and ECG monitoring and recording device according to the present invention.
Figure 4:
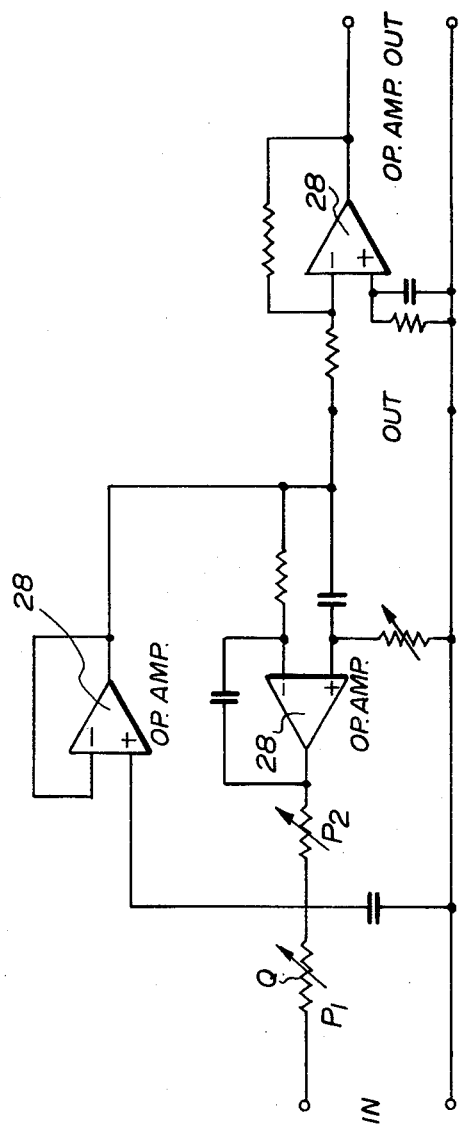
FIG. 4 is a circuit diagram of an example filter which may be used in the device of FIG. 3.

Turning to FIG. 3, a simple block diagram of the instrument is shown. Sounds picked up by condenser microphones 4 are converted to electric signals and passed, on separate audio channels, through amplifier 20 where they are amplified, for example, about 65 dB. Amplifier 20 is a low noise dual channel amplifier with a channel separation greater than 60 dB. The signal is then fed to a frequency analyzer 24 which is made up of four Butterworth (trademark) active band pass filters 26 with a variable center frequency between 150 HZ and 1,000 HZ. Each filter has a variable quality factor Q and a variable band width. As can be seen from FIG. 4, the active filter band width can be changed with potentiometer $P_1$ without shifting the center frequency. This property is desirable in such applications as the present. The mid-frequency of the band pass filter can be changed using potentiometer $P_2$ independently without changing the band width. All operative amplifiers 28 of the filter are of the 741 type.

The output signal from each filter 26 is multiplexed at multiplexer 30 and fed to the input A of oscilloscope 32. This permits a simultaneous and continuous display of each signals channel on a single channel of the oscilloscope. The multiplexer is essentially two analog switches (FET and CMOS) which are turned on and off by the Q and Q of the oscillator 34. Oscillator 34 is an astable multivibrator built from two NAND gates and RC coupling. The output of the A stable multivibrator is fed to the buffer before it is fed to multiplexer 30. That output is also fed to transformer 36 and rectifier 38 to provide a DC power source of about 1.5 volts to each condenser microphone. The ground of this DC supply is isolated from the common ground of the instrument (see FIG. 5).

Figure 5:
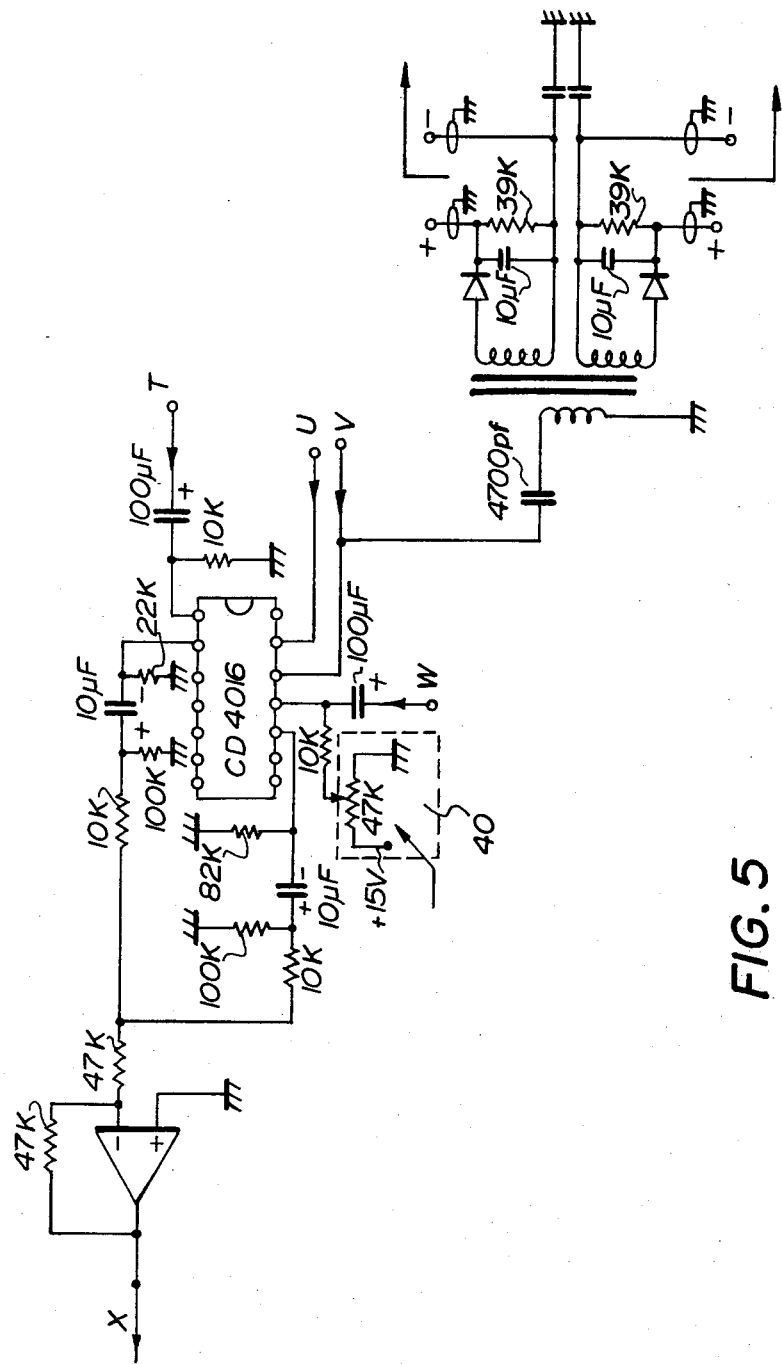
FIG. 5 is a circuit diagram of an example multiplexer and DC power supply unit used in the device as illustrated in FIG. 3.

In the circuit diagram of the multiplexer shown in FIG. 5, input from one of the channels from filter 26 or directly from amplifier 20 arrives at T. The signal from Q of oscillator 34 arrives at U whereas the signal from Q arrives at V. Input from the other channel, either from the other filter 26 or directly from amplifier 20 arrives at W. Adjustment means 40 is provided to permit baseline separation of the two channels on the scope of the oscilloscope cathode ray tube. The signal from multiplexer 30 to the oscilloscope leaves at X.

It will be noted from FIG. 3 that the output signal of each filter 26 is also fed to a buffer amplifier 42 which provides in turn an output signal to a chart recorder 44.

Another DC power supply with isolated ground is generated through rectifier 48 to supply power to the ECG amplifier (FIG. 2) 50. The DC voltage is 2.5 volts (DC). The input to the ECG amplifier is 2 leads with a floating ground. This achieves a high common mode rejection.

The output of the ECG amplifier is filtered at 52 and is connected to the second channel (input B) of the oscilloscope and displayed simultaneously with the signal on input 1. The ECG is supplied and displayed so that the sound signals picked up by the condenser microphones can be correlated with the ECG signal, as illustrated in FIG. 6.

Figure 6:
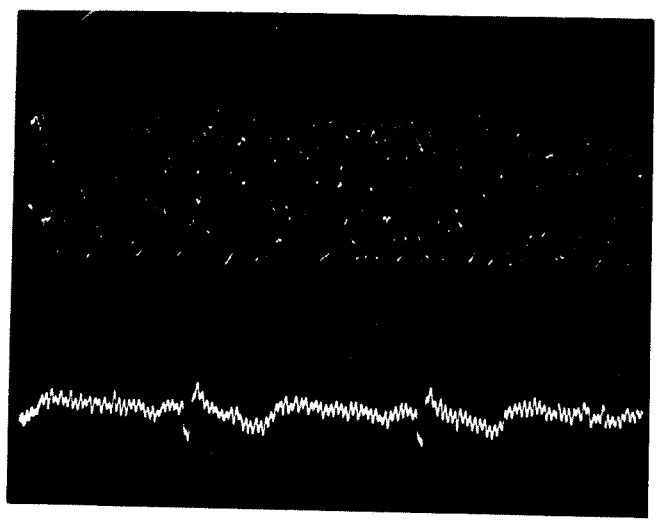
FIG. 6 is a plot of a signal spectrum of a device according to the present invention from a patient monitored on an oscilloscope.

In FIG. 6, the upper edge of the upper plot is formed by the signals from the channel from one of the ear microphones, while the lower edge of that plot is formed by the channel from the other ear microphone. The lower plot line is the ECG plot, showing two T-waves.

The circuits of this device may be built from integrated circuits and the circuitry may be sufficiently small in size so that it can be incorporated within a two-input portable oscilloscope.

In operation, if it is desired to monitor or diagnose a patient with audible tinnitus or the like, the ear piece 10 on each microphone tip is inserted in the auditory canal of the patient and held tightly in each ear with the adjustable screws 8 shown in FIG. 1. The ECG electrodes (2 electrodes) are attached to the patient's chest. Upon activation, the selector switch for each channel is turned to a position which by-passes the filters 26 and recordings without filter are observed on the oscilloscope and on the chart recorder. After recordings without filter have been monitored, the selector switch of each channel is turned to a filter position and filtered information is then recorded and analyzed.

Thus it is apparent that there has been provided, in accordance with the present invention, a device capable of continuous recording of vascular and mascular tinnitus using tymphanic phonocephalographic techniques, that fully satisfies the objects, aims and advantages set forth above. While the invention has been described in conjunction with example embodiments thereof, it is evident that many alternatives, modifications and variations will be apparent to those skilled in the art in light of the foregoing description. Accordingly it is intended to embrace all such alternatives, modifications and variations as fall within the spirit and broad scope of the appended claims.

I claim as my invention:

1. A device for monitoring, amplifying and frequency analyzing sounds from the surface and cavities of the head comprising:
   (i) a microphone of sufficient sensitivity to detect such sound, the microphone being secured to an ear piece of a shape which permits insertion thereof into a patient's ear and transfer of sounds within the ear to the microphone;
   (ii) a head band to which the microphone is secured, to support the microphone in position with the ear piece inserted in the ear of the patient;

(iii) an amplifier electrically associated with the microphone for increasing the output signals from the microphone;
(iv) a frequency analyzer electrically connected to the amplifier whereby signals from the amplifier are passed to the frequency analyzer in order to filter and analyze those signals;
(v) display means electrically connected to the analyzer and to the amplifier to receive and display filtered or unfiltered signals.

2. A device according to claim 1, wherein a pair of microphones are provided, one for each ear of a patient, and having the amplifier electrically connected to each microphone and to the analyzer to increase the output signals from each microphone.

3. A device according to claim 2, further provided with a multiplexing oscillator electrically connected to receive from both of the ear insertable microphones the amplified signals filtered by the frequency analyzer or unfiltered signals directly from the amplifier, and wherein the display means comprises an oscilloscope and is electrically connected to receive the output of the multiplexing oscillator.

4. A device according to claim 3, wherein the display means additionally comprises a chart recorder.

5. A device according to claim 3, wherein the multiplexing oscillator is further provided with means to supply the voltage to operate the ear insertable microphones.

6. A device according to claim 3, further provided with an ECG pickup and signal amplification means therefor, the output from the ECG amplification means being connected to the input of the oscilloscope to simultaneously display the ECG signal with that from the ear insertable microphones so that the signals can be correlated.

7. A device according to claim 6, wherein a further filter is electrically connected to the ECG amplification means to filter the signal therefrom, and wherein the power supply to the ECG amplification means is provided with an isolated ground.

8. A device according to claim 2, wherein the amplifier associated with each microphone increases the output signal about 65 dB.

9. A device according to claim 2, wherein the frequency analyzer comprises active passband filters having a variable quality factor (Q) and a variable center frequency between 150 HZ and 1,000 HZ.

10. A device according to claim 2 wherein adjustable fastening means secure the microphones to the headband, whereby the insertion of the ear piece of each microphone into the ears of the patient may be adjusted.

11. A method for continuously, non-invasively monitoring and recording vascular and muscular tinnitus for a patient which comprises the steps of:
(i) monitoring in each of the patient's ears sounds emanating from the surface and cavities of the head;
(ii) converting the sounds into electric signals on a separate channel, one for each ear;
(iii) amplifying and filtering the electric signals;
(iv) multiplexing the amplified, filtered signals from both channels;
(v) displaying the filtered or unfiltered signals on a display or recording means.

12. A method according to claim 11, wherein the patient's ECG is simultaneously monitored and displayed on the display or recording means.

* * * * *